United States Patent
Sode

(10) Patent No.: US 7,329,519 B2
(45) Date of Patent: Feb. 12, 2008

(54) GLUCOSE DEHYDROGENASE β SUBUNIT AND DNA ENCODING THE SAME

(76) Inventor: Koji Sode, 1-13-16, Minami, Meguro-ku, Tokyo 152-0013 (JP)

(\*) Notice: Subject to any disclaimer, the term of this patent is extended or adjusted under 35 U.S.C. 154(b) by 0 days.

(21) Appl. No.: 11/443,562

(22) Filed: May 31, 2006

(65) Prior Publication Data

US 2006/0211094 A1    Sep. 21, 2006

Related U.S. Application Data

(62) Division of application No. 10/511,796, filed as application No. PCT/JP03/05375 on Apr. 25, 2003, now Pat. No. 7,094,585.

(30) Foreign Application Priority Data

Apr. 26, 2002  (JP) .............................. 2002-125353

(51) Int. Cl.
*C12N 9/18*    (2006.01)
*C12N 5/00*    (2006.01)
*C12N 1/20*    (2006.01)
*C12P 21/06*   (2006.01)
*C07H 21/04*   (2006.01)

(52) U.S. Cl. ..................... 435/190; 435/69.1; 435/325; 435/146; 435/252.8; 435/320.1; 435/252.3; 435/197; 536/23.2

(58) Field of Classification Search ..................... None
See application file for complete search history.

(56) References Cited

U.S. PATENT DOCUMENTS

2004/0245121 A1  12/2004  Nagakawa et al.

FOREIGN PATENT DOCUMENTS

| EP | 0 477 788 A1 | 4/1992 |
|---|---|---|
| EP | 1 331 272 A1 | 7/2003 |
| WO | WO 02/36779 | 5/2002 |

OTHER PUBLICATIONS

Whisstock, et al. Quarterly Rev. Biophy. 2003, 36, pp. 307-340.*
Brenner, et al. "Assessing Sequence Comparison Methods with Reliable Structurally Identified Distant Evolutionary Relationships," *Proc. Natl. Acad. Sci. USA*, vol. 95, No. 11, pp. 6073-6078, May 1998.
Kondo, et al. "Characterization of the Genes Encoding the Three-Component Membrane-Bound Alcohol Dehyrogenase from *Gluconobacter suboxydans* and Their Expression in *Acetobacter pasteurianus*," *Applied and Environmental Microbiology*, vol. 63, No. 3, pp. 1131-1138, Mar. 1997.
Supplementary European Search Report dated Oct. 19, 2005.
Inose, et al. "Cloning and Expression of the Gene Encoding Catalytic Subunit of Thermostable Glucose Dehydrogenase from *Burkholderia cepacia* in *Escherichia coli*," *Biochimica et Biophysica Acta*, 1645(2), pp. 133-138, Feb. 2003.
Sode, et al. "A Novel Thermostable Glucose Dehydrogenase Varying Temperature Properties by Altering its Quatemary Structures," *Enzyme and Microbial Technology*, vol. 19, pp. 82-95, 1996.
Yamazaki, et al. "Increased Thermal Stability of Glucose Dehydrogenase by Cross-Linking Chemical Modification," *Biotechnology Letters*, vol. 21, pp. 199-202, 1999.
Yamazaki, et al. "Subunit Analyses of a Novel Thermostable Glucose Dehydrogenase Showing Different Temperature Properties According to its Quaternary Structure," *Applied Biochemistry and Biotechnology*, vol. 77-79, pp. 325-335, 1999.
International Search Report, issud to a related foreign application, (date not avail.).

\* cited by examiner

*Primary Examiner*—Rebecca E. Prouty
*Assistant Examiner*—Md. Younus Meah
(74) *Attorney, Agent, or Firm*—Knobbe, Martens, Olson & Bear, LLP

(57) ABSTRACT

A DNA fragment encoding a β subunit is obtained by inverse PCR using primers designed based on the nucleotide sequnece of a N-terminal signal sequence region of a GDH β subunit derived from *Burkholderia cepacia* KS1 strain.

12 Claims, No Drawings

SEQUENCE LISTING

```
<160> NUMBER OF SEQ ID NOS: 19

<210> SEQ ID NO 1
<211> LENGTH: 2467
<212> TYPE: DNA
<213> ORGANISM: Burkhorderia cepacia
<220> FEATURE:
<221> NAME/KEY: CDS
<222> LOCATION: (258)...(761)
<220> FEATURE:
<221> NAME/KEY: CDS
<222> LOCATION: (764)...(2380)
<220> FEATURE:
<221> NAME/KEY: CDS
<222> LOCATION: (2386)...(2466)

<400> SEQUENCE: 1
aagctttctg tttgattgca cgcgattcta accgagcgtc tgtgaggcgg aacgcgacat      60
gcttcgtgtc gcacacgtgt cgcgccgacg acacaaaaat gcagcgaaat ggctgatcgt     120
tacgaatggc tgacacattg aatggactat aaaaccattg tccgttccgg aatgtgcgcg     180
```

```
tacatttcag gtccgcgccg attttttgaga aatatcaagc gtggttttcc cgaatccggt    240
gttcgagaga aggaaac atg cac aac gac aac act ccc cac tcg cgt cgc       290
                   Met His Asn Asp Asn Thr Pro His Ser Arg Arg
                    1               5                       10 cac ggc gac gca gcc gca tca ggc atc acg cgg cgt caa tgg ttg caa      338
His Gly Asp Ala Ala Ala Ser Gly Ile Thr Arg Arg Gln Trp Leu Gln
            15                  20                  25 ggc gcg ctg gcg ctg acc gca gcg ggc ctc acg ggt tcg ctg aca ttg      386
Gly Ala Leu Ala Leu Thr Ala Ala Gly Leu Thr Gly Ser Leu Thr Leu
        30                  35                  40 cgg gcg ctt gca gac aac ccc ggc act gcg ccg ctc gat acg ttc atg      434
Arg Ala Leu Ala Asp Asn Pro Gly Thr Ala Pro Leu Asp Thr Phe Met
    45                  50                  55 acg ctt tcc gaa tcg ctg acc ggc aag aaa ggg ctc agc cgc gtg atc      482
Thr Leu Ser Glu Ser Leu Thr Gly Lys Lys Gly Leu Ser Arg Val Ile
60                  65                  70                  75 ggc gag cgc ctg ctg cag gcg ctg cag aag ggc tcg ttc aag acg gcc      530
Gly Glu Arg Leu Leu Gln Ala Leu Gln Lys Gly Ser Phe Lys Thr Ala
                80                  85                  90 gac agc ctg ccg cag ctc gcc ggc gcg ctc gcg tcc ggt tcg ctg acg      578
Asp Ser Leu Pro Gln Leu Ala Gly Ala Leu Ala Ser Gly Ser Leu Thr
            95                  100                 105 cct gaa cag gaa tcg ctc gca ctg acg atc ctc gag gcc tgg tat ctc      626
Pro Glu Gln Glu Ser Leu Ala Leu Thr Ile Leu Glu Ala Trp Tyr Leu
        110                 115                 120 ggc atc gtc gac aac gtc gtg att acg tac gag gaa gca tta atg ttc      674
Gly Ile Val Asp Asn Val Val Ile Thr Tyr Glu Glu Ala Leu Met Phe
    125                 130                 135 ggc gtc gtg tcc gat acg ctc gtg atc cgt tcg tat tgc ccc aac aaa      722
Gly Val Val Ser Asp Thr Leu Val Ile Arg Ser Tyr Cys Pro Asn Lys
140                 145                 150                 155 ccc ggc ttc tgg gcc gac aaa ccg atc gag agg caa gcc tg atg gcc       769
Pro Gly Phe Trp Ala Asp Lys Pro Ile Glu Arg Gln Ala     Met Ala
                160                 165                     170 gat acc gat acg caa aag gcc gac gtc gtc gtc gtt gga tcg ggt gtc      817
Asp Thr Asp Thr Gln Lys Ala Asp Val Val Val Val Gly Ser Gly Val
            175                 180                 185 gcg ggc gcg atc gtc gcg cat cag ctc gcg atg gcg ggc aag gcg gtg      865
Ala Gly Ala Ile Val Ala His Gln Leu Ala Met Ala Gly Lys Ala Val
        190                 195                 200 atc ctg ctc gaa gcg ggc ccg cgc atg ccg cgc tgg gaa atc gtc gag      913
Ile Leu Leu Glu Ala Gly Pro Arg Met Pro Arg Trp Glu Ile Val Glu
    205                 210                 215 cgc ttc cgc aat cag ccc gac aag atg gac ttc atg gcg ccg tac ccg      961
Arg Phe Arg Asn Gln Pro Asp Lys Met Asp Phe Met Ala Pro Tyr Pro
220                 225                 230 tcg agc ccc tgg gcg ccg cat ccc gag tac ggc ccg ccg aac gac tac     1009
Ser Ser Pro Trp Ala Pro His Pro Glu Tyr Gly Pro Pro Asn Asp Tyr
235                 240                 245                 250 ctg atc ctg aag ggc gag cac aag ttc aac tcg cag tac atc cgc gcg     1057
Leu Ile Leu Lys Gly Glu His Lys Phe Asn Ser Gln Tyr Ile Arg Ala
            255                 260                 265 gtg ggc ggc acg acg tgg cac tgg gcc gcg tcg gcg tgg cgc ttc att     1105
Val Gly Gly Thr Thr Trp His Trp Ala Ala Ser Ala Trp Arg Phe Ile
        270                 275                 280 ccg aac gac ttc aag atg aag agc gtg tac ggc gtc ggc cgc gac tgg     1153
Pro Asn Asp Phe Lys Met Lys Ser Val Tyr Gly Val Gly Arg Asp Trp
    285                 290                 295 ccg atc cag tac gac gat ctc gag ccg tac tat cag cgc gcg gag gaa     1201
```

```
Pro Ile Gln Tyr Asp Asp Leu Glu Pro Tyr Tyr Gln Arg Ala Glu Glu
    300                 305                 310 gag ctc ggc gtg tgg ggc ccg ggc ccc gag gaa gat ctg tac tcg ccg      1249
Glu Leu Gly Val Trp Gly Pro Gly Pro Glu Glu Asp Leu Tyr Ser Pro
315                 320                 325                 330 cgc aag cag ccg tat ccg atg ccg ctg ccg ttg tcg ttc aac gag          1297
Arg Lys Gln Pro Tyr Pro Met Pro Pro Leu Pro Leu Ser Phe Asn Glu
                335                 340                 345 cag acc atc aag acg gcg ctg aac aac tac gat ccg aag ttc cat gtc      1345
Gln Thr Ile Lys Thr Ala Leu Asn Asn Tyr Asp Pro Lys Phe His Val
            350                 355                 360 gtg acc gag ccg gtc gcg cgc aac agc cgc ccg tac gac ggc cgc ccg      1393
Val Thr Glu Pro Val Ala Arg Asn Ser Arg Pro Tyr Asp Gly Arg Pro
        365                 370                 375 act tgt tgc ggc aac aac aac tgc atg ccg atc tgc ccg atc ggc gcg      1441
Thr Cys Cys Gly Asn Asn Asn Cys Met Pro Ile Cys Pro Ile Gly Ala
    380                 385                 390 atg tac aac ggc atc gtg cac gtc gag aag gcc gaa cgc gcc ggc gcg      1489
Met Tyr Asn Gly Ile Val His Val Glu Lys Ala Glu Arg Ala Gly Ala
395                 400                 405                 410 aag ctg atc gag aac gcg gtc gtc tac aag ctc gag acg ggc ccg gac      1537
Lys Leu Ile Glu Asn Ala Val Val Tyr Lys Leu Glu Thr Gly Pro Asp
                415                 420                 425 aag cgc atc gtc gcg gcg ctc tac aag gac aag acg ggc gcc gag cat      1585
Lys Arg Ile Val Ala Ala Leu Tyr Lys Asp Lys Thr Gly Ala Glu His
            430                 435                 440 cgc gtc gaa ggc aag tat ttc gtg ctc gcc gcg aac ggc atc gag acg      1633
Arg Val Glu Gly Lys Tyr Phe Val Leu Ala Ala Asn Gly Ile Glu Thr
        445                 450                 455 ccg aag atc ctg ctg atg tcc gcg aac cgc gat ttc ccg aac ggt gtc      1681
Pro Lys Ile Leu Leu Met Ser Ala Asn Arg Asp Phe Pro Asn Gly Val
    460                 465                 470 gcg aac agc tcg gac atg gtc ggc cgc aac ctg atg gac cat ccg ggc      1729
Ala Asn Ser Ser Asp Met Val Gly Arg Asn Leu Met Asp His Pro Gly
475                 480                 485                 490 acc ggc gtg tcg ttc tat gcg agc gag aag ctg tgg ccg ggc cgc ggc      1777
Thr Gly Val Ser Phe Tyr Ala Ser Glu Lys Leu Trp Pro Gly Arg Gly
                495                 500                 505 ccg cag gag atg acg tcg ctg atc ggt ttc cgc gac ggt ccg ttc cgc      1825
Pro Gln Glu Met Thr Ser Leu Ile Gly Phe Arg Asp Gly Pro Phe Arg
            510                 515                 520 gcg acc gaa gcg gcg aag aag atc cac ctg tcg aac ctg tcg cgc atc      1873
Ala Thr Glu Ala Ala Lys Lys Ile His Leu Ser Asn Leu Ser Arg Ile
        525                 530                 535 gac cag gag acg cag aag atc ttc aag gcc ggc aag ctg atg aag ccc      1921
Asp Gln Glu Thr Gln Lys Ile Phe Lys Ala Gly Lys Leu Met Lys Pro
    540                 545                 550 gac gag ctc gac gcg cag atc cgc gac cgt tcc gca cgc tac gtg cag      1969
Asp Glu Leu Asp Ala Gln Ile Arg Asp Arg Ser Ala Arg Tyr Val Gln
555                 560                 565                 570 ttc gac tgc ttc cac gaa atc ctg ccg caa ccc gag aac cgc atc gtg      2017
Phe Asp Cys Phe His Glu Ile Leu Pro Gln Pro Glu Asn Arg Ile Val
                575                 580                 585 ccg agc aag acg gcg acc gat gcg atc ggc att ccg cgc ccc gag atc      2065
Pro Ser Lys Thr Ala Thr Asp Ala Ile Gly Ile Pro Arg Pro Glu Ile
            590                 595                 600 acg tat gcg atc gac gac tac gtg aag cgc ggc gcc gcg cat acg cgc      2113
Thr Tyr Ala Ile Asp Asp Tyr Val Lys Arg Gly Ala Ala His Thr Arg
        605                 610                 615
```

```
gag gtc tac gcg acc gcc gcg aag gtg ctc ggc ggc acg gac gtc gtg      2161
Glu Val Tyr Ala Thr Ala Ala Lys Val Leu Gly Gly Thr Asp Val Val
    620                 625                 630 ttc aac gac gaa ttc gcg ccg aac aat cac atc acg ggc tcg acg atc      2209
Phe Asn Asp Glu Phe Ala Pro Asn Asn His Ile Thr Gly Ser Thr Ile
635                 640                 645                 650 atg ggc gcc gat gcg cgc gac tcc gtc gtc gac aag gac tgc cgc acg      2257
Met Gly Ala Asp Ala Arg Asp Ser Val Val Asp Lys Asp Cys Arg Thr
                655                 660                 665 ttc gac cat ccg aac ctg ttc att tcg agc agc gcg acg atg ccg acc      2305
Phe Asp His Pro Asn Leu Phe Ile Ser Ser Ser Ala Thr Met Pro Thr
            670                 675                 680 gtc ggt acc gta aac gtg acg ctg acg atc gcc gcg ctc gcg ctg cgg      2353
Val Gly Thr Val Asn Val Thr Leu Thr Ile Ala Ala Leu Ala Leu Arg
        685                 690                 695 atg tcg gac acg ctg aag aag gaa gtc tgacc gtg cgg aaa tct act ctc    2403
Met Ser Asp Thr Leu Lys Lys Glu Val     Val Arg Lys Ser Thr Leu
700                 705                         710 act ttc ctc atc gcc ggc tgc ctc gcg ttg ccg ggc ttc gcg cgc gcg      2451
Thr Phe Leu Ile Ala Gly Cys Leu Ala Leu Pro Gly Phe Ala Arg Ala
    715                 720                 725 gcc gat gcg gcc gat c                                                2467
Ala Asp Ala Ala Asp
730

<210> SEQ ID NO 2
<211> LENGTH: 168
<212> TYPE: PRT
<213> ORGANISM: Burkhorderia cepacia

<400> SEQUENCE: 2

Met His Asn Asp Asn Thr Pro His Ser Arg Arg His Gly Asp Ala Ala
1               5                   10                  15

Ala Ser Gly Ile Thr Arg Arg Gln Trp Leu Gln Gly Ala Leu Ala Leu
            20                  25                  30

Thr Ala Ala Gly Leu Thr Gly Ser Leu Thr Leu Arg Ala Leu Ala Asp
        35                  40                  45

Asn Pro Gly Thr Ala Pro Leu Asp Thr Phe Met Thr Leu Ser Glu Ser
    50                  55                  60

Leu Thr Gly Lys Lys Gly Leu Ser Arg Val Ile Gly Glu Arg Leu Leu
65                  70                  75                  80

Gln Ala Leu Gln Lys Gly Ser Phe Lys Thr Ala Asp Ser Leu Pro Gln
                85                  90                  95

Leu Ala Gly Ala Leu Ala Ser Gly Ser Leu Thr Pro Glu Gln Glu Ser
            100                 105                 110

Leu Ala Leu Thr Ile Leu Glu Ala Trp Tyr Leu Gly Ile Val Asp Asn
        115                 120                 125

Val Val Ile Thr Tyr Glu Glu Ala Leu Met Phe Gly Val Val Ser Asp
    130                 135                 140

Thr Leu Val Ile Arg Ser Tyr Cys Pro Asn Lys Pro Gly Phe Trp Ala
145                 150                 155                 160

Asp Lys Pro Ile Glu Arg Gln Ala
                165

<210> SEQ ID NO 3
<211> LENGTH: 539
<212> TYPE: PRT
<213> ORGANISM: Burkhorderia cepacia
```

<400> SEQUENCE: 3

```
Met Ala Asp Thr Asp Thr Gln Lys Ala Asp Val Val Val Gly Ser
  1               5                  10                  15

Gly Val Ala Gly Ala Ile Val Ala His Gln Leu Ala Met Ala Gly Lys
             20                  25                  30

Ala Val Ile Leu Leu Glu Ala Gly Pro Arg Met Pro Arg Trp Glu Ile
             35                  40                  45

Val Glu Arg Phe Arg Asn Gln Pro Asp Lys Met Asp Phe Met Ala Pro
         50                  55                  60

Tyr Pro Ser Ser Pro Trp Ala Pro His Pro Glu Tyr Gly Pro Pro Asn
 65                  70                  75                  80

Asp Tyr Leu Ile Leu Lys Gly Glu His Lys Phe Asn Ser Gln Tyr Ile
                 85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
            115                 120                 125

Asp Trp Pro Ile Gln Tyr Asp Asp Leu Glu Pro Tyr Tyr Gln Arg Ala
130                 135                 140

Glu Glu Glu Leu Gly Val Trp Gly Pro Gly Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
                180                 185                 190

His Val Val Thr Glu Pro Val Ala Arg Asn Ser Arg Pro Tyr Asp Gly
                195                 200                 205

Arg Pro Thr Cys Cys Gly Asn Asn Asn Cys Met Pro Ile Cys Pro Ile
        210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
                260                 265                 270

Glu His Arg Val Glu Gly Lys Tyr Phe Val Leu Ala Ala Asn Gly Ile
            275                 280                 285

Glu Thr Pro Lys Ile Leu Leu Met Ser Ala Asn Arg Asp Phe Pro Asn
        290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
        355                 360                 365

Arg Ile Asp Gln Glu Thr Gln Lys Ile Phe Lys Ala Gly Lys Leu Met
    370                 375                 380

Lys Pro Asp Glu Leu Asp Ala Gln Ile Arg Asp Arg Ser Ala Arg Tyr
385                 390                 395                 400

Val Gln Phe Asp Cys Phe His Glu Ile Leu Pro Gln Pro Glu Asn Arg
                405                 410                 415
```

```
Ile Val Pro Ser Lys Thr Ala Thr Asp Ala Ile Gly Ile Pro Arg Pro
        420                 425                 430

Glu Ile Thr Tyr Ala Ile Asp Asp Tyr Val Lys Arg Gly Ala Ala His
        435                 440                 445

Thr Arg Glu Val Tyr Ala Thr Ala Ala Lys Val Leu Gly Gly Thr Asp
        450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ala Thr Met
        500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val
        530                 535
```

<210> SEQ ID NO 4
<211> LENGTH: 27
<212> TYPE: PRT
<213> ORGANISM: Burkhorderia cepacia

<400> SEQUENCE: 4

```
Val Arg Lys Ser Thr Leu Thr Phe Leu Ile Ala Gly Cys Leu Ala Leu
1               5                   10                  15

Pro Gly Phe Ala Arg Ala Ala Asp Ala Ala Asp
            20                  25
```

<210> SEQ ID NO 5
<211> LENGTH: 28
<212> TYPE: DNA
<213> ORGANISM: Artificial Sequence
<220> FEATURE:
<223> OTHER INFORMATION: Artificial sequence; primer

<400> SEQUENCE: 5
cccaagcttg ggccgatacc gatacgca                                    28

<210> SEQ ID NO 6
<211> LENGTH: 28
<212> TYPE: DNA
<213> ORGANISM: Artificial Sequence
<220> FEATURE:
<223> OTHER INFORMATION: Artificial sequence; primer

<400> SEQUENCE: 6
gagaagcttt ccgcacggtc agacttcc                                    28

<210> SEQ ID NO 7
<211> LENGTH: 27
<212> TYPE: DNA
<213> ORGANISM: Artificial Sequence
<220> FEATURE:
<223> OTHER INFORMATION: Artificial sequence; primer

<400> SEQUENCE: 7
catgccatgg cacacaacga caacact                                     27

<210> SEQ ID NO 8
<211> LENGTH: 31
<212> TYPE: DNA

-continued

```
<213> ORGANISM: Artificial Sequence
<220> FEATURE:
<223> OTHER INFORMATION: Artificial sequence; primer

<400> SEQUENCE: 8
cccaagcttg ggtcagactt ccttcttcag c                           31

<210> SEQ ID NO 9
<211> LENGTH: 16
<212> TYPE: PRT
<213> ORGANISM: Burkhorderia cepacia

<400> SEQUENCE: 9

Ala Asp Ala Ala Asp Pro Ala Leu Val Lys Arg Gly Glu Tyr Leu Ala
 1               5                  10                  15

<210> SEQ ID NO 10
<211> LENGTH: 25
<212> TYPE: PRT
<213> ORGANISM: Artificial Sequence
<220> FEATURE:
<223> OTHER INFORMATION: Artificial sequence; consensus
<220> FEATURE:
<221> NAME/KEY: UNSURE
<222> LOCATION: (6)...(6)
<223> OTHER INFORMATION: Xaa=unknown
<220> FEATURE:
<221> NAME/KEY: UNSURE
<222> LOCATION: (17)...(19)
<223> OTHER INFORMATION: Xaa=unknown
<220> FEATURE:
<221> NAME/KEY: UNSURE
<222> LOCATION: (22)...(22)
<223> OTHER INFORMATION: Xaa=unknown

<400> SEQUENCE: 10

Ala Asp Ala Ala Asp Xaa Ala Leu Val Lys Arg Gly Glu Tyr Leu Ala
 1               5                  10                  15

Xaa Xaa Xaa Asp Cys Xaa Ala Cys His
            20                  25

<210> SEQ ID NO 11
<211> LENGTH: 2410
<212> TYPE: DNA
<213> ORGANISM: Burkhorderia cepacia
<220> FEATURE:
<221> NAME/KEY: CDS
<222> LOCATION: (673)...(1950)

<400> SEQUENCE: 11
gatggaccac ccgggcaccg gcgtgtcgtt ctacgcgaac gagaagctgt ggccgggccg     60
cggcccgcag gatatgacgt cgctgatcgg tttccgcgac ggcccgttcc gcgcgaccga    120
agccgcgaag aagatccatc tgtcgaacat gtcccgcatc aaccaggaga cgcagaagat    180
cttcaaggcc ggcaaactga tgaagcacga ggagctcgac gcgcagatcc gcgaccgttc    240
cgcgcgctac gtgcagttcg actgcttcca cgagattctg ccgcagcccg agaaccgcat    300
cgtgccgagc aagacggcca ccgacgcgat cgggatcccg cgccccgaga tcacgtatgc    360
gatcgacgat tacgtgaagc gcggcgccgt gcacacgcgc gaggtctacg cgacggccgc    420
gaaggtgctg ggcggcaccg acgtcgtctt caacgacgag ttcgcgccga caaccacat    480 cacgggcgcg aggatcatgg gcgcggatgc acgcgactcg gtcgtcgaca aggactgccg    540
cacgttcgac catccgaacc tgttcctctc gagcagctcg acgatgccga ccgtcggtac    600
ggtgaacgtg acgctgacga tcgcggcgct cgcgctgcgg atgtcggaca cgctgaagaa    660
```

```
ggaagtctga cc gtg cgg aaa tct act ctc acc ttc ctc ctc gcc ggc tgc       711
              Val Arg Lys Ser Thr Leu Thr Phe Leu Leu Ala Gly Cys
               1               5                  10 ctc gcg ctg ccc ggc ctc gca cgc gcg gcc gat tcg gcc gat ccg gcg         759
Leu Ala Leu Pro Gly Leu Ala Arg Ala Ala Asp Ser Ala Asp Pro Ala
 15              20                  25 cat gtc aag cgc ggc gaa tac ctc gcc gtc gcg ggc gac tgc atg gca         807
His Val Lys Arg Gly Glu Tyr Leu Ala Val Ala Gly Asp Cys Met Ala
 30              35                  40                  45 tgc cac acc gcg aag ggc ggc aag ccg ttc gcg ggc ggc ctc ggc atg         855
Cys His Thr Ala Lys Gly Gly Lys Pro Phe Ala Gly Gly Leu Gly Met
             50                  55                  60 ccg gtg ccg atg ctc ggc aag atc tat acg agc aac atc aca ccg gat         903
Pro Val Pro Met Leu Gly Lys Ile Tyr Thr Ser Asn Ile Thr Pro Asp
                65                  70                  75 ccc gat acc ggc atc ggc aac tgg acg ttc gag gac ttc gag cgc gcg         951
Pro Asp Thr Gly Ile Gly Asn Trp Thr Phe Glu Asp Phe Glu Arg Ala
         80                  85                  90 gtg cgg cac ggc gta tcg aag aac ggc gac aac ctg tac ccg gcg atg         999
Val Arg His Gly Val Ser Lys Asn Gly Asp Asn Leu Tyr Pro Ala Met
 95              100                 105 ccg tac gtg tcg tac gcg aag atc aac gac gac gac gtg caa gcg ctg        1047
Pro Tyr Val Ser Tyr Ala Lys Ile Asn Asp Asp Asp Val Gln Ala Leu
110                 115                 120                 125 tac gcg tac ttc atg cac ggc gtc gaa ccg gtc aag cag gcg ccg ccg        1095
Tyr Ala Tyr Phe Met His Gly Val Glu Pro Val Lys Gln Ala Pro Pro
                130                 135                 140 aag aac gag atc ccc gcg ctg ctg agc atg cgc tgg ccg ctg aag atc        1143
Lys Asn Glu Ile Pro Ala Leu Leu Ser Met Arg Trp Pro Leu Lys Ile
            145                 150                 155 tgg aac tgg ctg ttc ctg aag gac ggc gtg tac cag ccg aag ccc gag        1191
Trp Asn Trp Leu Phe Leu Lys Asp Gly Val Tyr Gln Pro Lys Pro Glu
        160                 165                 170 cag agc gcc gag tgg aac cgc ggc gcc tat ctc gtg cag ggc ctc gcg        1239
Gln Ser Ala Glu Trp Asn Arg Gly Ala Tyr Leu Val Gln Gly Leu Ala
175                 180                 185 cac tgc agc acg tgc cac acg ccg cgc ggc atc gcg atg cag gag aag        1287
His Cys Ser Thr Cys His Thr Pro Arg Gly Ile Ala Met Gln Glu Lys
190                 195                 200                 205 tcg ctc gac gaa acg ggc ggc agc ttc ctg tcg ggc tcg gtg ctc gcg        1335
Ser Leu Asp Glu Thr Gly Gly Ser Phe Leu Ser Gly Ser Val Leu Ala
                210                 215                 220 ggc tgg gac ggc tac aac atc acg tcc gac ccg aac gcg ggg atc ggc        1383
Gly Trp Asp Gly Tyr Asn Ile Thr Ser Asp Pro Asn Ala Gly Ile Gly
            225                 230                 235 ggc tgg acg cag cag cag ctc gtc cag tac ctg cgc acc ggc agc gtg        1431
Gly Trp Thr Gln Gln Gln Leu Val Gln Tyr Leu Arg Thr Gly Ser Val
        240                 245                 250 ccg ggc ctc gcg cag gcg gcc ggc ccg atg gcc gag gcg atc gag cac        1479
Pro Gly Leu Ala Gln Ala Ala Gly Pro Met Ala Glu Ala Ile Glu His
255                 260                 265 agc ttc tcg aag atg acc gaa gcc gac atc ggc ggc ccg atg gcc gag        1527
Ser Phe Ser Lys Met Thr Glu Ala Asp Ile Gly Gly Pro Met Ala Glu
270                 275                 280                 285 gcg atc gag cac agc ttc tcg aag atg acc gaa gcc gac atc ggc cgc        1575
Ala Ile Glu His Ser Phe Ser Lys Met Thr Glu Ala Asp Ile Gly Arg
                290                 295                 300 tcg tcg tgg ggc aag ccg gcc gag gat ggc ctg aag ctg cgc ggc gtc        1623
Ser Ser Trp Gly Lys Pro Ala Glu Asp Gly Leu Lys Leu Arg Gly Val
```

```
                   305                 310                 315
gcg ctc gcg tcg tcg ggc atc gat ccg gca ccg ctg tat ctc ggc aac    1671
Ala Leu Ala Ser Ser Gly Ile Asp Pro Ala Pro Leu Tyr Leu Gly Asn
            320                 325                 330 tgc gcg acc tgc cac cag atg cag ggc aag ggc acg ccg gac ggt tac    1719
Cys Ala Thr Cys His Gln Met Gln Gly Lys Gly Thr Pro Asp Gly Tyr
        335                 340                 345 tac ccg ccg ttg ttc cac aac tcg acg gtc ggc gcg tcg aat ccg acc    1767
Tyr Pro Pro Leu Phe His Asn Ser Thr Val Gly Ala Ser Asn Pro Thr
350                 355                 360                 365 aac ctc gtg cag gtg atc ctg aac ggc gtg cag cgc aag gcc ggc agc    1815
Asn Leu Val Gln Val Ile Leu Asn Gly Val Gln Arg Lys Ala Gly Ser
                370                 375                 380 gag gac gtc ggg atg ccc gcg ttc cgc cac gag ctg tcg gat gcg cag    1863
Glu Asp Val Gly Met Pro Ala Phe Arg His Glu Leu Ser Asp Ala Gln
            385                 390                 395 atc gcc gcg ctg acg aac tac ctg acg ggg cag ttc ggc aat ccg gcc    1911
Ile Ala Ala Leu Thr Asn Tyr Leu Thr Gly Gln Phe Gly Asn Pro Ala
        400                 405                 410 gcg aag gtg acc gag cag gac gtc gcg aag ctg cgc tga aacgcggcac    1960
Ala Lys Val Thr Glu Gln Asp Val Ala Lys Leu Arg   *
    415                 420                 425 gcggcgaggc agggcaacaa tagaaaagag gaggagcaca gcacatcggg cgggccccga   2020
tgccggttgt tgcagagcgg gacgggcggc gcaggcggtc gcccgtcctg gttcacaggc   2080
aatccggtgc gcgcacgccg cgcatcgttt tcgttgatcg agaccatgac accgaaccaa   2140
ccgtttctcg cgtcccagcg cgatgtgctg ctgctgctgt cccgaatcct gctcgtgatc   2200
ctgttcgtga tgttcggctg gaagaagatt atcgacttct ccggtacgat cgcgttcatg   2260
ggcagcgagg gcgcgccggc gccgatcatc tcggcggcga tctccgtcgt gatggagctc   2320
atcgtcggga ttgcgatcct cgtcggtttc cagacgcggc cgctcgcgct gttgcttgcg   2380
ctgtacacga tcggtaccgg catcatcggc                                    2410

<210> SEQ ID NO 12
<211> LENGTH: 425
<212> TYPE: PRT
<213> ORGANISM: Burkhorderia cepacia

<400> SEQUENCE: 12

Val Arg Lys Ser Thr Leu Thr Phe Leu Leu Ala Gly Cys Leu Ala Leu
 1               5                  10                  15

Pro Gly Leu Ala Arg Ala Ala Asp Ser Ala Asp Pro Ala His Val Lys
            20                  25                  30

Arg Gly Glu Tyr Leu Ala Val Ala Gly Asp Cys Met Ala Cys His Thr
        35                  40                  45

Ala Lys Gly Gly Lys Pro Phe Ala Gly Gly Leu Gly Met Pro Val Pro
    50                  55                  60

Met Leu Gly Lys Ile Tyr Thr Ser Asn Ile Thr Pro Asp Pro Asp Thr
65                  70                  75                  80

Gly Ile Gly Asn Trp Thr Phe Glu Asp Phe Glu Arg Ala Val Arg His
                85                  90                  95

Gly Val Ser Lys Asn Gly Asp Asn Leu Tyr Pro Ala Met Pro Tyr Val
            100                 105                 110

Ser Tyr Ala Lys Ile Asn Asp Asp Val Gln Ala Leu Tyr Ala Tyr
        115                 120                 125

Phe Met His Gly Val Glu Pro Val Lys Gln Ala Pro Pro Lys Asn Glu
```

-continued

```
            130                 135                 140
Ile Pro Ala Leu Leu Ser Met Arg Trp Pro Lys Ile Trp Asn Trp
145                 150                 155                 160

Leu Phe Leu Lys Asp Gly Val Tyr Gln Pro Lys Pro Glu Gln Ser Ala
                165                 170                 175

Glu Trp Asn Arg Gly Ala Tyr Leu Val Gln Gly Leu Ala His Cys Ser
                180                 185                 190

Thr Cys His Thr Pro Arg Gly Ile Ala Met Gln Glu Lys Ser Leu Asp
                195                 200                 205

Glu Thr Gly Gly Ser Phe Leu Ser Gly Ser Val Leu Ala Gly Trp Asp
210                 215                 220

Gly Tyr Asn Ile Thr Ser Asp Pro Asn Ala Gly Ile Gly Gly Trp Thr
225                 230                 235                 240

Gln Gln Gln Leu Val Gln Tyr Leu Arg Thr Gly Ser Val Pro Gly Leu
                245                 250                 255

Ala Gln Ala Ala Gly Pro Met Ala Glu Ala Ile Glu His Ser Phe Ser
                260                 265                 270

Lys Met Thr Glu Ala Asp Ile Gly Gly Pro Met Ala Glu Ala Ile Glu
                275                 280                 285

His Ser Phe Ser Lys Met Thr Glu Ala Asp Ile Gly Arg Ser Ser Trp
                290                 295                 300

Gly Lys Pro Ala Glu Asp Gly Leu Lys Leu Arg Gly Val Ala Leu Ala
305                 310                 315                 320

Ser Ser Gly Ile Asp Pro Ala Pro Leu Tyr Leu Gly Asn Cys Ala Thr
                325                 330                 335

Cys His Gln Met Gln Gly Lys Gly Thr Pro Asp Gly Tyr Tyr Pro Pro
                340                 345                 350

Leu Phe His Asn Ser Thr Val Gly Ala Ser Asn Pro Thr Asn Leu Val
                355                 360                 365

Gln Val Ile Leu Asn Gly Val Gln Arg Lys Ala Gly Ser Glu Asp Val
                370                 375                 380

Gly Met Pro Ala Phe Arg His Glu Leu Ser Asp Ala Gln Ile Ala Ala
385                 390                 395                 400

Leu Thr Asn Tyr Leu Thr Gly Gln Phe Gly Asn Pro Ala Ala Lys Val
                405                 410                 415

Thr Glu Gln Asp Val Ala Lys Leu Arg
                420                 425
```

<210> SEQ ID NO 13
<211> LENGTH: 27
<212> TYPE: DNA
<213> ORGANISM: Artificial Sequence
<220> FEATURE:
<223> OTHER INFORMATION: Artificial sequence; primer

<400> SEQUENCE: 13
tgcaccgtgc ggaaatctac tctcact                      27

<210> SEQ ID NO 14
<211> LENGTH: 27
<212> TYPE: DNA
<213> ORGANISM: Artificial Sequence
<220> FEATURE:
<223> OTHER INFORMATION: Artificial sequence; primer

<400> SEQUENCE: 14
acttccttct tcagcgtgtc cgacatc                      27

<210> SEQ ID NO 15
<211> LENGTH: 1441
<212> TYPE: DNA
<213> ORGANISM: Burkhorderia cepacia
<220

```
gcg cag gcg gcc ggg ccg atg gcc gag gcg gtc gag cac agc ttc tcg         936
Ala Gln Ala Ala Gly Pro Met Ala Glu Ala Val Glu His Ser Phe Ser
        260                 265                 270 aag atg acc gaa gcg gac atc ggt gcg atc gcc acg tac gtc cgc acg         984
Lys Met Thr Glu Ala Asp Ile Gly Ala Ile Ala Thr Tyr Val Arg Thr
            275                 280                 285 gtg ccg gcc gtt gcc gac agc aac gcg aag cag ccg cgg tcg tcg tgg        1032
Val Pro Ala Val Ala Asp Ser Asn Ala Lys Gln Pro Arg Ser Ser Trp
290                 295                 300 ggc aag ccg gcc gag gac ggg ctg aag ctg cgc ggt gtc gcg ctc gcg        1080
Gly Lys Pro Ala Glu Asp Gly Leu Lys Leu Arg Gly Val Ala Leu Ala
305                 310                 315                 320 tcg tcg ggc atc gat ccg gcg cgg ctg tat ctc ggc aac tgc gcg acg        1128
Ser Ser Gly Ile Asp Pro Ala Arg Leu Tyr Leu Gly Asn Cys Ala Thr
            325                 330                 335 tgc cac cag atg cag ggc aag ggc acg ccg gac ggc tat tac ccg tcg        1176
Cys His Gln Met Gln Gly Lys Gly Thr Pro Asp Gly Tyr Tyr Pro Ser
            340                 345                 350 ctg ttc cac aac tcc acc gtc ggc gcg tcg aat ccg tcg aac ctc gtg        1224
Leu Phe His Asn Ser Thr Val Gly Ala Ser Asn Pro Ser Asn Leu Val
            355                 360                 365 cag gtg atc ctg aac ggc gtg cag cgc aag atc ggc agc gag gat atc        1272
Gln Val Ile Leu Asn Gly Val Gln Arg Lys Ile Gly Ser Glu Asp Ile
370                 375                 380 ggg atg ccc gct ttc cgc tac gat ctg aac gac gcg cag atc gcc gcg        1320
Gly Met Pro Ala Phe Arg Tyr Asp Leu Asn Asp Ala Gln Ile Ala Ala
385                 390                 395                 400 ctg acg aac tac gtg acc gcg cag ttc ggc aat ccg gcg gcg aag gtg        1368
Leu Thr Asn Tyr Val Thr Ala Gln Phe Gly Asn Pro Ala Ala Lys Val
            405                 410                 415 acg gag cag gac gtc gcg aag ctg cgc tga catagtcggg cgcgccgaca         1418
Thr Glu Gln Asp Val Ala Lys Leu Arg *
            420                 425 cggcgcaacc gataggacag gag                                              1441

<210> SEQ ID NO 16
<211> LENGTH: 425
<212> TYPE: PRT
<213> ORGANISM: Burkhorderia cepacia

<400> SEQUENCE: 16

Val Arg Lys Ser Thr Leu Thr Phe Leu Ile Ala Gly Cys Leu Ala Leu
1               5                   10                  15

Pro Gly Phe Ala Arg Ala Ala Asp Ala Ala Asp Pro Ala Leu Val Lys
            20                  25

```
Phe Met His Gly Val Glu Pro Val Lys Gln Ala Pro Pro Lys Asn Glu
    130                 135                 140

Ile Pro Ala Leu Leu Ser Met Arg Trp Pro Leu Lys Ile Trp Asn Trp
145                 150                 155                 160

Leu Phe Leu Lys Asp Gly Pro Tyr Gln Pro Lys Pro Ser Gln Ser Ala
            165                 170                 175

Glu Trp Asn Arg Gly Ala Tyr Leu Val Gln Gly Leu Ala His Cys Ser
        180                 185                 190

Thr Cys His Thr Pro Arg Gly Ile Ala Met Gln Glu Lys Ser Leu Asp
        195                 200                 205

Glu Thr Gly Gly Ser Phe Leu Ala Gly Ser Val Leu Ala Gly Trp Asp
    210                 215                 220

Gly Tyr Asn Ile Thr Ser Asp Pro Asn Ala Gly Ile Gly Ser Trp Thr
225                 230                 235                 240

Gln Gln Gln Leu Val Gln Tyr Leu Arg Thr Gly Ser Val Pro Gly Val
            245                 250                 255

Ala Gln Ala Ala Gly Pro Met Ala Glu Ala Val Glu His Ser Phe Ser
        260                 265                 270

Lys Met Thr Glu Ala Asp Ile Gly Ala Ile Ala Thr Tyr Val Arg Thr
        275                 280                 285

Val Pro Ala Val Ala Asp Ser Asn Ala Lys Gln Pro Arg Ser Ser Trp
    290                 295                 300

Gly Lys Pro Ala Glu Asp Gly Leu Lys Leu Arg Gly Val Ala Leu Ala
305                 310                 315                 320

Ser Ser Gly Ile Asp Pro Ala Arg Leu Tyr Leu Gly Asn Cys Ala Thr
            325                 330                 335

Cys His Gln Met Gln Gly Lys Gly Thr Pro Asp Gly Tyr Tyr Pro Ser
        340                 345                 350

Leu Phe His Asn Ser Thr Val Gly Ala Ser Asn Pro Ser Asn Leu Val
        355                 360                 365

Gln Val Ile Leu Asn Gly Val Gln Arg Lys Ile Gly Ser Glu Asp Ile
    370                 375                 380

Gly Met Pro Ala Phe Arg Tyr Asp Leu Asn Asp Ala Gln Ile Ala Ala
385                 390                 395                 400

Leu Thr Asn Tyr Val Thr Ala Gln Phe Gly Asn Pro Ala Ala Lys Val
            405                 410                 415

Thr Glu Gln Asp Val Ala Lys Leu Arg
        420                 425

<210> SEQ ID NO 17
<211> LENGTH: 5
<212> TYPE: PRT
<213> ORGANISM: Artificial Sequence
<220> FEATURE:
<223> OTHER INFORMATION: Artificial sequence; heme binding motif
<220> FEATURE:
<221> NAME/KEY: UNSURE
<222> LOCATION: (2)...(3)
<223> OTHER INFORMATION: Xaa=unknown

<400> SEQUENCE: 17

Cys Xaa Xaa Cys His
 1               5

<210> SEQ ID NO 18
<211> LENGTH: 27
<212> TYPE: DNA
<213> ORGANISM: Artificial Sequence
```

```
-continued

<220> FEATURE:
<223> OTHER INFORMATION: Artificial sequence; primer

<400> SEQUENCE: 18
catgccatgg cacacaacga caacact                                    27

<210> SEQ ID NO 19
<211> LENGTH: 31
<212> TYPE: DNA
<213> ORGANISM: Artificial Sequence
<220> FEATURE:
<223> OTHER INFORMATION: Artificial sequence; primer

<400> SEQUENCE: 19
cccaagcttg ggtcagactt ccttcttcag c                               31
```

GLUCOSE DEHYDROGENASE β SUBUNIT AND DNA ENCODING THE SAME

RELATED APPLICATION

This application is a divisional application of U.S. application Ser. No. 10/511,796, filed Oct. 19, 2004, now U.S. Pat. No. 7,094,585, which is the U.S. National Phase under 35 U.S.C. § 371 of International Application PCT/JP03/05375, filed Apr. 25, 2003, which was published in a language other than English, which claims priority of JP 2002-125353, filed Apr. 26, 2002.

TECHNICAL FIELD

The present invention relates to cytochrome C that constitutes a glucose dehydrogenase β subunit, to a DNA encoding the cytochrome C, and to their utilization. The glucose dehydrogenase is useful for a glucose sensor using an enzyme electrode or the like.

BACKGROUND ART

Biosensors using an enzyme that specifically reacts with a particular substrate are being actively developed in various industrial fields. As for a glucose sensor, which is one of the biosensors, in particular, measurement methods and devices utilizing such methods are being actively developed mainly in medical fields. For example, the glucose sensor has a history of about 40 years since Clark and Lyons first reported about a biosensor including glucose oxidase and an oxygen electrode in combination in 1962 (L. c. Clark, J. and Lyonas, C. "Electrode systems for continuous monitoring in cardiovascular surgery." Ann. n. y. Acad. Sci., 105: 20-45).

Thus, the adoption of glucose oxidase as an enzyme for the glucose sensor has a long history. This is because glucose oxidase shows high substrate specificity for glucose and superior thermal stability, this enzyme can further be produced in a large scale, and its production cost is lower than those of other enzymes. The high substrate specificity means that this enzyme does not react with a saccharide other than glucose, and this leads to an advantage that accurate measurement can be achieved without error in measurement values. Further, the superior thermal stability means that problems concerning denaturation of the enzyme and inactivation of its enzymatic activity due to heat can be prevented, and this leads to an advantage that accurate measurement can be performed over a long period of time.

However, although glucose oxidase has advantages as described above, it has a problem that the enzyme is affected by dissolved oxygen and this affects measurement results.

Meanwhile, in addition to glucose oxidase, a glucose sensor utilizing glucose dehydrogenase (hereinafter referred to as "glucose dehydrogenase" or "GDH") has also been developed. This enzyme is also found in microorganisms. For example, there are known glucose dehydrogenase derived from *Bacillus* (EC 1.1.1.47) and glucose dehydrogenase derived from *Cryptococcus* (EC 1.1.1.119).

The former glucose dehydrogenase (EC 1.1.1.47) is an enzyme that catalyzes a reaction of β-D-glucose+NAD(P)$^+$→D-δ-gluconolactone+NAD(P)H+H$^+$, and the latter glucose dehydrogenase (EC 1.1.1.119) is an enzyme that catalyzes a reaction of D-glucose+NADP$^+$→D-δ-gluconolactone+NADPH+H$^+$. The aforementioned glucose dehydrogenases derived from microorganisms are already marketed.

These glucose dehydrogenases have an advantage that they are not affected by dissolved oxygen in a measurement sample. This leads to an advantage that accurate measurement can be achieved without causing errors in measurement results even when the measurement is performed in an environment in which the oxygen partial pressure is low, or a high-concentration sample requiring a large amount of oxygen is used for the measurement.

However, although conventional glucose dehydrogenase is not affected by dissolved oxygen, it has problems of poor thermal stability and substrate specificity poorer than that of glucose oxidase. For an enzyme which is used in a sensor, an enzyme that overcomes disadvantages of both of glucose oxidase and glucose dehydrogenase has been desired.

The inventors of the present invention reported results of their studies about GDH using samples collected from soil near hot springs in Sode, K., Tsugawa, W., Yamazaki, T., Watanabe, M., Ogasawara, N., and Tanaka, M., Enzyme Microb. Technol., 19, 82-85 (1996); Yamazaki, T., Tsugawa, W. and Sode, K., Appli. Biochemi. and Biotec., 77-79/0325 (1999); and Yamazaki, T., Tsugawa, W. and Sode, K., Biotec. Lett., 21, 199-202 (1999). The microorganisms in those samples produce a coenzyme-binding GDH, and the enzymologic properties such as optimum reaction temperature, thermal stability, and substrate specificity have already been clear (See the aforementioned documents). This enzyme is a hetero oligomeric enzyme that is constituted by a catalyst subunit having a high thermal resistance (α subunit), an electron transferring subunit (β subunit), and γ subunit having an unknown function, and the activity peaks thereof are observed at 45° C. and 75° C., respectively. Further, the γ and α subunit genes have been cloned, and it has been clarified that the aforementioned microorganism belongs to *Burkholderia cepacia*, and the N-terminal amino acid sequence of the β subunit has been clarified (Ken Inose, Tokyo Agricultural Engineering University Master's Thesis (2001)). However, the structure of the β subunit gene has not been reported.

DISCLOSURE OF THE INVENTION

An object of the present invention is to provide a DNA encoding a GDH β subunit of a microorganism belonging to the genus *Burkholderia* and a method of using the DNA.

The inventors of the present invention have further advanced the study on GDH of *Burkholderia cepacia* KS1 strain and were successful in isolating a DNA encoding a GDH β subunit, thereby completing the present invention.

That is, the present invention can be described as follows.

(1) A protein defined in the following (A) or (B):

(A) a protein which has at least the amino acid sequence comprising amino acids 23 to 425 of SEQ ID NO: 16;

(B) a protein which has at least the amino acid sequence comprising amino acids 23 to 425 of SEQ ID NO: 16 including substitution, deletion, insertion or addition of 1 to 20 amino acid residues.

(2) A DNA encoding a protein defined in the following (A) or (B):

(A) a protein which has at least the amino acid sequence consisting of amino acids 23 to 425 of SEQ ID NO: 16;

(B) a protein which has at least the amino acid sequence comprising amino acids 23 to 425 of SEQ ID NO: 16 including substitution, deletion, insertion or addition of 1 to 20 amino acid residues.

(3) The DNA according to item (2), in which the DNA is defined in the following (a) or (b):

(a) a DNA including the nucleotide sequnece consisting of nucleotides 187 to 1398 of SEQ ID NO: 15;

(b) a DNA which is hybridizable with the nucleotide sequnece consisting of nucleotides 187 to 1398 of SEQ ID NO: 15 under stringent conditions.

(4) The DNA according to item (3), further including the nucleotide sequnece consisting of nucleotides 121 to 187 of SEQ ID NO: 15.

(5) A recombinant vector including a DNA according to any one of items (2) to (4).

(6) A transformant transformed with a DNA according to any one of items (2) to (4) or the recombinant vector according to item (5).

(7) A method of producing a glucose dehydrogenase β subunit, including culturing the transformant according to item (6) to produce a glucose dehydrogenase β subunit as an expression product of the DNA, and collecting the produced β subunit.

(8) The DNA according to item (3) or (4), further including the nucleotide sequnece encoding an α subunit and a γ subunit of glucose dehydrogenase of *Burkholderia cepacia*.

(9) A recombinant vector including the DNA according to item (8).

(10) A transformant transformed with the DNA according to item (8) or the recombinant vector according to item (9).

(11) A method of producing a glucose dehydrogenase complex, including culturing the transformant according to item

(10) to produce a glucose dehydrogenase complex as an expression product of the DNA, and collecting the produced complex.

BEST MODE FOR CARRYING OUT THE INVENTION

Hereinafter, the present invention will be described in detail.

The inventors of the present invention have searched and isolated a DNA encoding a GDH β subunit of *Burkholderia cepacia* KS1 strain. The aforementioned strain was deposited at International Patent Organism Depositary, National Institute of Advanced Industrial Science and Technology (Central 6, 1-1-1, Higashi 1-chome, Tsukuba-shi, Ibaraki-ken, Japan, postal code: 305-8566) on Sep. 25, 2000 and received a microorganism accession number of FERM BP-7306. In the present specification, the DNA encoding the GDH β subunit is sometimes referred to as the DNA of the present invention, "β subunit structural gene", or simply "β subunit gene".

The inventors of the present invention have confirmed that GDH produced by *Burkholderia cepacia* KS1 strain is a polymeric protein containing an α subunit, a β subunit, and a γ subunit. The protein of the present invention corresponds to: the β subunit out of these subunits. Spectrophotometric analyses for GDH indicate that the absorption wavelength of an oxidized GDH resembles the absorption wavelengths of alcohol dehydrogenase and aldehyde dehydrogenase of *Gluconobacter* sp. and *Acetobacter* sp. that are composed of dehydrogenase cytochrome complex, and this absorption is lost by heat treatment. This fact and the difference in optimum reaction temperature of the GDH between presence and absence of the β subunit as described below have suggested that the β subunit is composed of cytochrome C.

Physical and chemical properties of the above GDH are shown below.

(1) Function: the enzyme catalyzes dehydrogenation reaction of glucose.

(2) The enzyme consists of subunits showing a molecular weight of about 60 kDa and a molecular weight of about 43 kDa in SDS-polyacrylamide gel electrophoresis under a reducing condition.

(3) The enzyme shows a molecular weight of about 380 kDa in gel filtration chromatography using TSK Gel G3000SW (Manufactured by Tosoh Corporation).

(4) Optimal reaction temperature: around 45° C. (Tris-HCl buffer, pH 8.0). Physical and chemical properties of an a-subunit alone are shown below.

(1)' The protein has a glucose dehydrogenase activity.

(2)' The protein shows a molecular weight of about 60 kDa in SDS-polyacrylamide gel electrophoresis under a reducing condition.

(3)' Optimal reaction temperature: around 75° C. (Tris-HCl buffer, pH 8.0).

The β subunit can be obtained together with other subunits from a culture of *Burkholderia cepacia* KS1 strain by purifying a GDH complex using GDH activity as an index. The GDH activity can be measured in the same manner as in the known GDH activity measurement. Specifically, the measurement can be performed as follows. A 10 mM potassium phosphate buffer (pH 7.0) containing 594 μM 1-methoxyphenazine methosulfate (mPMS) and 5.94 μM 2,6-dichlorophenol indophenol (DCIP) are added to an enzyme sample and glucose as a substrate, and the mixture is incubated at 37° C. A change in the absorbance of DCIP at 600 nm is traced using a spectrophotometer, and the decrease rate in the absorbance is defined as an enzyme reaction rate.

In addition, since the nucleotide sequence of a gene encoding the β subunit (SEQ ID NO: 15) has been determined by the present invention, the β subunit can also be produced by expressing a DNA having the nucleotide sequence or a DNA encoding the same amino acid sequence as the amino acid sequence encoded by this DNA in a suitable host. The amino acid sequence that can be encoded by the open reading frame (ORF) of SEQ ID NO: 15 is shown in SEQ ID NO: 16. The N-terminal amino acid sequence of the β subunit determined from the protein was identical to the amino acids 23 to 38 of SEQ ID NO: 16. Therefore, the amino acids 1 to 22 are presumed to be a signal peptide. Note that although amino acid residue 1 is described as Val in SEQ ID NOs: 15 and 16, it has a high possibility to be Met and it also has a possibility to be dropped after the translation.

Results of homology search on the aforementioned amino acid sequence by BLAST indicated overall high homologies; 65% homology with a cytochrome C subunit of oxidoreductase dehydrogenase derived form *Ralstonia solanacearum*, 48% homology with a cytochrome C subunit of sorbitol dehydrogenase derived from *Gluconobacter oxydans*, 44% homology with a cytochrome C subunit of gluconic acid dehydrogenase derived from *Eriwinia cypripedii*, and 55.7% homology on the nucleotide sequnece level or a 46.4% homology on the amino acid level with a cytochrome C subunit of 2-keto-gluconic acid dehydrogenase derived from *Pantoea citrea*. Furthermore, the amino acid sequences of these cytochromes C reserved a hem-linking motif (SEQ ID NO: 18). These facts show that the β subunit of the present invention is cytochrome C.

The β subunit of the present invention may be a protein having the amino acid sequence consisting of the amino acids 23 to 425 of SEQ ID NO: 16 including substitution, deletion, insertion, or addition of 1 to 20, preferably 1 to 10, more preferably 1 to 5 amino acid residues in the amino acid sequence so long as it can function as a GDH β subunit. Note that the term "functions as a GDH β subunit" means "functions as cytochrome C without deteriorating the enzyme activity of the GDH".

The DNA of the present invention is a DNA that encodes the aforementioned β subunit and can be obtained from, for example, *Burkholderia cepacia* KS1 strain. The DNA of the present invention has been isolated from the chromosomal DNA of *Burkholderia cepacia* KS1 strain in the course of completion of the present invention. The DNA of the present invention can be obtained, for example, by PCR using primers having nucleotide sequences of SEQ ID NOs: 13 and 14 and the chromosomal DNA of *Burkholderia cepacia* KS1 strain as a template. In addition, since the nucleotide sequence of the DNA of the present invention and the amino acid sequence encoded by the nucleotide sequence have been clarified by the present invention, the DNA of the present invention can also be obtained by performing chemical synthesis based on these sequences. Furthermore, the DNA of the present invention can be obtained from the chromosomal DNA of *Burkholderia cepacia* KS1 strain by hybridization using the oligonucleotide prepared based on the aforementioned sequences as probes. Similarly, variants can be obtained from strains other than *Burkholderia cepacia*.

The DNA of the present invention may be one encoding a protein having the amino acid sequence consisting of the amino acids 23 to 425 of SEQ ID NO: 16 or one having the amino acid sequence including substitution, deletion, insertion, or addition of 1 to 20, preferably 1 to 10, more preferably 1 to 5 amino acid residues and encoding a protein that functions as a GDH β subunit.

Specifically, the DNA of the present invention includes a DNA having the nucleotide sequnece consisting of the nucleotides 187 to 1398 of SEQ ID NO: 15. Further, the DNA of the present invention may be a DNA that hybridizes with SEQ ID NO: 15 or a probe that can be prepared form this sequence under stringent conditions and encodes a protein that can function as a β subunit. The stringent conditions include those conditions whereby DNAs having a 70% or more, preferably 80% or more, more preferably 90% or more homology to each other hybridize, specifically conditions of 1×SSC, 0.1% SDS, and 60° C.

The GDH β subunit can be produced by culturing a transformant that harbors the DNA of the present invention or a recombinant vector containing the DNA of the present invention to produce the GDH β subunit as an expression product of the DNA, and by collecting the GDH β subunit from the microorganism cells or the culture medium. In this case, the DNA encoding the GDH β subunit of the present invention may be expressed together with a DNA encoding an α subunit or further a DNA encoding a γ subunit to produce a GDH complex. A DNA fragment that sequentially encodes the γ subunit and the α subunit can be obtained by PCR using primers having nucleotide sequences of SEQ ID NOs: 18 and 19.

Examples of the microorganism that produces the GDH β subunit or the GDH complex include: enterobacteria including *Escherichia coli*; Gram negative bacteria such as *Pseudomonas* and *Gluconobacter*; Gram positive bacteria including bacteria belonging to the genus *Bacillus* such as *Bacillus subtilis*; yeasts such as *Saccharomyces* cerevisiae; and molds such as *Aspergillus niger*. However, the microorganism is not limited to these and any microorganism may be used so long as it is a host microorganism suitable for the production of foreign proteins.

Vectors that are used for cloning or expressing the DNA of the present invention are suitably those constructed for gene recombination from plasmids or phages that can autonomously replicate in host microorganisms. Examples of vectors for *E. coli* include pBR322, pUC18, pUC118, pUC19, pUC119, pTrc99A, pBluescript, or SuperCosI, which is a cosmid. Transfer of the DNA from the vector that has been used in cloning the DNA of the present invention to other recombinant vectors suitable for expression, etc. can be readily performed by recovering the DNA of the present invention from a recombinant vector containing the DNA of the present invention with a restriction enzyme or by the PCR method and ligating it with a vector fragment. Furthermore, transformation of microorganisms with these vectors can be performed by the competent cell method by treatment with calcium for bacteria belonging to the genus *Escherichia*, the protoplast method for bacteria belonging to the genus *Bacillus*, the KU method or the KUR method for yeasts, and the micromanipulation method for molds and so forth. In addition, the electroporation method can also be used widely.

Selection of host microorganisms based on presence or absence of introduction of the target recombinant vector therein may be performed by using a chemical resistance marker of the vector containing the target DNA and the like. For example, a microorganism that can grow in a selective medium based on a chemical resistance marker and produces GDH may be selected.

As for the culture method of the transformant, culture conditions may be selected by considering nutritional and physiological properties of the host. In many cases, liquid culture is performed. It is industrially advantageous to perform aeration culture with shaking.

As nutrients of the medium, those usually used for culture of microorganisms may be widely used. As carbon sources, any assimilable carbon compounds may be used, and examples of the compounds to be used include glucose, sucrose, lactose, maltose, lactose, molasses, pyruvic acid and so forth. Furthermore, as nitrogen sources, any utilizable nitrogen compounds may be used, and examples of the compounds to be used include peptone, meat extracts, yeast extracts, casein hydrolysates, soybean cake alkaline extracts and so forth. In addition, phosphate, carbonate, sulfate, salts of magnesium, calcium, potassium, iron, manganese, zinc and so forth, particular amino acids, particular vitamins and so forth are used as required.

Although the culture temperature can be appropriately changed in a range in which a bacteria grows and produces the protein of the present invention, it is preferably about 20° C. to 42° C. The culture time somewhat varies depending on the conditions. However, the culture may be completed at an appropriate time estimated to give the maximum GDH yield, and the culture time is usually about 12 to 72 hours. Although pH of the medium may be appropriately changed in a range in which a bacteria grows and produces the protein of the present invention, it is preferably in the range of about pH 6.0 to 9.0.

The culture medium containing cells of the microorganism producing the protein of the present invention in the culture can be collected and utilized as they are. However, when the protein of the present invention exists in the culture medium, the culture medium is usually separated into the solution containing the protein of the present invention and microorganism cells by filtration, centrifugation or the like in a conventional manner and then used. When the protein of the present invention exists in the cells, the cells are collected from the obtained culture by means of filtration, centrifugation or the like, and then disrupted by a mechanical method or an enzymatic method such as use of lysozyme. Further, a chelating agent such as EDTA and a surfactant are added to the cell to solubilize the protein of the present invention, as required, followed by isolation and collection as an aqueous solution.

Protein may be precipitated from the thus-obtained protein-containing solution by, for example, vacuum concentration, membrane concentration, salting out with ammonium sulfate, sodium sulfate or the like, or a fractional precipitation with a hydrophilic organic solvent such as methanol, ethanol, and acetone. Further, heat treatment and isoelectric point treatment are also effective purification means. Then, purification can be performed by a suitable combination of gel filtration using an adsorbent, gel filtration agent, etc., absorption chromatography, ion exchange chromatography and affinity chromatography to obtain a purified protein of the present invention.

A purified enzyme preparation can be obtained by isolation and purification based on column chromatography. Although the purified enzyme preparation is preferably purified to such an extent that a single band is obtained in electrophoresis (SDS-PAGE), it may contain an α-subunit or a γ-subunit.

The thus-obtained purified enzyme can be powdered by, for example, lyophilization, vacuum drying, spray drying or the like and distributed.

The GDH complex consisting of a β-subunit, an α-subunit, or whenever required, a γ-subunit of the present invention, or transformants containing those, may be used for an enzyme electrode of a glucose sensor. As the electrode, a carbon electrode, gold electrode, platinum electrode or the like may be used, and the GDH of the present invention is immobilized on the electrode. Examples of the method for immobilization include a method of using a crosslinking reagent, a method of entrapping the enzyme in a polymer matrix, a method of covering the enzyme with a dialysis membrane, methods of using a photocrosslinking polymer, conductive polymer, oxidation-reduction polymer or the like. Alternatively, the enzyme may be immobilized in a polymer or immobilized on an electrode by adsorption together with an electronic mediator of which typical examples are ferrocene and derivatives thereof, or these methods may be used in combination. Typically, the glucose dehydrogenase of the present invention is immobilized on a carbon electrode by using glutaraldehyde, and then glutaraldehyde is blocked by a treatment with a reagent having an amine group.

The glucose concentration can be measured as follows. A buffer is placed in a thermostatic cell, and a mediator is added thereto. Then, a constant temperature is maintained. As the mediator, potassium ferricyanide, phenazine methosulfate and so forth may be used. An electrode on which the enzyme of the present invention is immobilized is used as a working electrode, and a counter electrode (e.g., platinum electrode) and a reference electrode (e.g., Ag/AgCl electrode) are used. After a constant voltage is applied to the carbon electrode to obtain a steady-state current, a sample containing glucose is added thereto and the increase of the current is measured. The glucose concentration in the sample can be calculated according to a calibration curve produced by using glucose solutions having standard concentrations.

The GDH complex containing the β subunit of the present invention may be used as a component in an assay kit for saccharides such as glucose. Typically, the kit includes in addition to the GDH complex, a buffer necessary for the assay, a mediator, a standard solution of, for example, glucose for preparing a calibration curve, and a manual on the use of the kit. The enzyme according to the present invention may be provided in various forms, for example, as a freeze-dried reagent or as a solution in a suitable stock solution.

EXAMPLE

Hereinafter, the present invention will be described specifically with reference to examples.

Reference Example 1

Isolation of a Gene Encoding GDH α subunit of *Burkholderia cepacia* KS1 strain

<1> Preparation of chromosomal DNA from *Burkhorderia cepacia* KS1 strain.

A chromosomal gene was prepared from the Burkhorderia cepacia KS1 strain in a conventional manner. That is, the bacterial strain was shaken overnight at 34° C. by using a TL liquid medium (10 g of polypeptone, 1 g of yeast extract, 5 g of NaCl, 2 g of $KH_2PO_4$, 5 g of glucose in 1 L, pH 7.2). The grown cells were collected by centrifugation. The cells were suspended in a solution containing 10 mM NaCl, 20 mM Tris-HCl (pH 8.0), 1 mM EDTA, 0.5% SDS, and 100 µg/ml proteinase K and treated at 50° C. for 6 hours. This mixture was added to an equivalent volume of phenol-chloroform and stirred at room temperature for 10 minutes, and then the supernatant was collected by centrifugation. The supernatant was added to sodium acetate to give a final concentration of 0.3 M and overlaid with two-fold volume of ethanol to precipitate chromosomal DNA in the intermediate layer. The DNA was taken up with a glass rod, washed with 70% ethanol, and dissolved in an appropriate amount of TE buffer to obtain a chromosomal DNA solution.

<2> Determination of N-terminus amino acid sequence of GDH α-subunit

GDH purified in the same manner as in Example 2 was concentrated by lyophilization and separated by SDS-electrophoresis using 12.5% polyacrylamide to isolate the α-subunit. The thus obtained α-subunit was transferred onto a polyvinylidene fluoride membrane, and then the N-terminus amino acid sequence was determined by using an amino acid sequencer (PPSQ-10, manufactured by Shimadzu Corporation). As a result, it was found that the enzyme contained a peptide sequence consisting of 11 residues of the amino acid numbers 2 to 12 in the amino acid sequence of SEQ ID NO: 3.

<3> Cloning of a Gene Encoding α-subunit

The DNA prepared in <1> (1 µg) was subjected to partial digestion with a restriction enzyme Sau3AI, followed by treatment with calf intestinal alkaline phosphatase (CIAP). Separately, SuperCosI (obtained from Stratagene), which is a cosmid, was treated with BamHI, and the DNA fragment obtained by the partial digestion of the chromosomal DNA fragment derived from the α-15 strain with Sau3AI was introduced into SuperCosI by using T4 DNA ligase. *E. coli* XL-1 Blue MR (obtained from Stratagene) was transformed with the obtained recombinant DNA. A transformant was selected on an LB agar medium containing 10 µg/ml neomycin and 25 µg/ml ampicillin based on neomycin resistance and ampicillin resistance, which are antibiotic resistances on SuperCosI. The obtained transformant was cultured in the LB liquid medium. These transformant cells were collected and suspended in a reagent for measuring the GDH activity, and a clone was selected by using dehydrogenase activity for glucose as an index. As a result, one clone showing the glucose dehydrogenase activity was obtained.

<4> Subcloning

DNA fragments containing the-target gene were prepared from the cosmid, SuperCosI, containing the gene encoding the α-subunit obtained in <3>. The inserted gene fragments were cleaved from the cosmid by using a restriction enzyme NotI. These DNA fragments were treated with a restriction enzyme XbaI and introduced into a plasmid pUC18 digested with XbaI. The E. coli DH5 α-MCR strain was transformed with the plasmid pUC18 containing each inserted fragment, and colonies appeared on an LB agar medium containing 50 μg/ml of ampicillin were collected. The obtained transformants were cultured in the liquid LB medium, followed by examination for the GDH activity in the cells in the same manner as in <3>. As a result, a transformant showing the GDH activity was obtained. The plasmid was extracted from this transformant, and the inserted DNA fragment was analyzed. As a result, an insert of about 8.8 kbp was confirmed. This plasmid was designated as pKS1.

<5> Determination of the Nucleotide Sequence

Restriction enzyme analysis of the inserted DNA fragment in pKS1 was performed and the nucleotide sequence of the fragment was determined according to the conventional method. As a result, the sequence of the DNA encoding the N-terminus amino acid sequence of the α-subunit found in <2> was confirmed in this inserted DNA fragment, and an open reading frame containing this sequence was found. The determined nucleotide sequence and the amino acid sequence that can be encoded by this nucleotide sequence are as shown in SEQ ID NOs: 1 and 3. In the nucleotide sequence of SEQ NO: 1, nucleotide sequence downstream from nucletide number 2,386 encode amino acid sequence of SEQ NO: 4, and encode β-subunit.

Reference Example 2

Production of a GDH-α-subunit by Recomibinant E. coli.

Since the nucleotide sequence of the α-subunit was determined, a vector was prepared using the aforementioned structural gene of the α-subunit, and a transformant was further produced using this vector.

First, a gene to be inserted into the vector was prepared as follows.

Amplification was performed by PCR using a genome fragment derived from the KS1 strain as a template so that a desired restriction enzyme site is included. The following pair of oligonucleotide primers were used in PCR.

```
                                             (SEQ ID NO: 5)
(Forward)  5'-CCCAAGCTTGGGCCGATACCGATACGCA-3'

(SEQ ID NO: 6)
(Reverse)  5'-GAGAAGCTTTCCGCACGGTCAGACTTCC-3'
```

The gene amplified by PCR was digested with a restriction enzyme HindIII and inserted into an expression vector pFLAG-CTS (SIGMA) at its cloning site, HindIII site. The obtained plasmid was designated as pFLAG-CTS/α.

The E. coli DH5αMCR strain was transformed with the aforementioned plasmid pFLAG-CTS/α, and colonies appeared on the LB agar medium containing 50 μg/ml of ampicillin were collected.

Further, when the open reading frame of the pKS1 inserted fragment was searched in the upstream of the α-subunit, a structural gene consisting of 507 nucleotides encoding a polypeptide including 168 amino acid residues shown in SEQ ID NO: 2 (nucleotide numbers 258 to 761 in SEQ ID NO: 1) was newly found. This structural gene was considered to encode the γ-subunit.

Since it was found that the region encoding the γ-subunit existed upstream of the coding region of the α-subunit, a recombinant vector containing a gene having a polycistronic structure continuously including the γ-subunit and the α-subunit was produced, and a transformant introduced with this vector was constructed.

First, a gene to be inserted into the vector was prepared as follows.

Amplification was performed by PCR using a genome fragment derived from the KS1 strain continuously including the structural gene of the γ-subunit and the structural gene of the α-subunit as a template so that a desired restriction enzyme site is included. The following pair of oligonucleotide primers were used for PCR.

```
                                             (SEQ ID NO: 7)
(Forward)  5'-CATGCCATGGCACACAACGACAACACT-3'

(SEQ ID NO: 8)
(Reverse)  5'-CCCAAGCTTGGGTCAGACTTCCTTCTTCAGC-3'
```

The 5'-terminus and the 3'-terminus of the gene amplified by PCR were digested with NcoI and HindIII, respectively, and the gene was inserted into the vector pTrc99A (Pharmacia) at its cloning site, NcoI/HindIII site. The obtained plasmid was named pTrc99A/γ+α.

The E. coli DH5αMCR strain was transformed with the aforementioned plasmid pTrc99A/γ+α, and colonies appeared on the LB agar medium containing 50 μg/ml of ampicillin were collected.

The α-subunit was produced using the E. coli DH5αMCR strain transformed with each of the aforementioned plasmids pKS1, pFLAG-CTS/α and pTrc99A/γ+α. Each transformant was inoculated into 3 ml of the LB medium containing 50 μg/ml of ampicillin and cultured at 37° C. for 12 hours, and the cells were collected by centrifugation. The cells were disrupted by using a French press (1,500 kgf), and a membrane fraction (10 mM potassium phosphate buffer, pH 6.0) was isolated by ultracentrifugation (4° C., 160,400×g, 90 minutes).

Reference Example 3

Confirmation of GDH Activity

First, the GDH activity in each of the aforementioned membrane fractions was confirmed. Specifically, visual determination was performed by using 10 mM potassium phosphate buffer (pH 7.0) containing 594 μM of methylphenazine methosulfate (mPMS) and 5.94 μM of 2,6-dichlorophenolindopheol (DCIP). The results are shown below. The number of + represents the degree of color change from blue to colorless.

Membrane fraction of cultured transformant transformed with pFLAG-CTS/α:+

Membrane fraction of cultured transformant transformed with pKS1:++

Membrane fraction of cultured transformant transformed with pTrc99A/γ+α:+++

The GDH activity of the membrane fraction of the cultured transformant transformed with pFLAG-CTS/α containing only with the α-subunit was the lowest, and the GDH activity of the membrane fraction of the cultured transformant transformed with pTrc99A/γ+α, with which a vector was efficiently constructed, was the highest.

Although the α-subunit was expressed even in the transformant transformed with a vector using only the structural gene of the α-subunit, the α-subunit could be efficiently obtained by using a vector containing the structural gene of the γ-subunit and the structural gene of the α-subunit in combination.

Glucose was assayed using the glucose dehydrogenase of the present invention. The enzymatic activity of the glucose dehydrogenase (α-subunit) of the present invention was measured by using glucose having various concentrations. The GDH activity was measured in 10 mM potassium phosphate buffer (pH 7.0) containing 594 μM of methylphenazine methosulfate (mPMS) and 5.94 μM of 2,6-dichlorophenolindopheol (DCIP). An enzyme sample and glucose serving as a substrate were added thereto, followed by incubation at 37° C., and change in the absorbance of DCIP at 600 nm was monitored by using a spectrophotometer. The decreasing rate of the absorbance was measured as an enzymatic reaction rate. Glucose could be quantified in the range of 0.01 to 1.0 mM using the GDH of the present invention.

Example 1

Isolation of Gene Encoding a GDH β-subunit of Burkhorderia cepacia KS1 Strain

<1> Searching for Burkholderia cepacia KS1 strain GDH β subunit

GDH β subunit gene derived from KS1 strain was searched using Burkholderia cepacia J2315 strain genome database of Sanger Centre. Referring to a known N-terminal sequence of KS1 strain GDH β subunit (SEQ ID No: 9), there was designed an amino acid sequence (SEQ ID NO: 10) that has high homology to each cytochrome c subunit of an alcohol dehydrogenase derived from Acetobacter Sp. or Gluconobacter Sp. (Tamaki T. et al., Biochim Biophys Acta 1088 (2): 292-300 (1991), Matsushita K., et al., Biosci. Biotech. Biochem., 56, 304-310 (1992), Takemura H., et al., J Bacteriol, 175, 6857-66 (1993), Kondo K. et al., Appl Environ Microbiol, 63, 1131-8 (1997)); a gluconate dehydrogenase derived from Erwinia sp. or Pseudomonas sp. (Yum D Y, et al., J Bacteriol, 179, 6566-72 (1997), Matsushita K. et al., J Biochem, 85, 1173-81 (1979)); a sorbitol dehydrogenase derived from Gluconobacter sp. (Choi, E. S., et al., FEMS Microbiol. Lett., 125, 45-50 (1995)); and a 2-ketogluconate dehydrogenase derived from Erwinia sp. or Pantoea sp. (Pujol C J et al., J Bacteriol, 182, 2230-7, (2000)).

Based on the aforementioned amino acid sequence, gene sequences that encode amino acid sequences having high homologies have been searched from the aforementioned database of Burkholderia cepacia J2315 strain by BLAST. Then, the obtained five sequences were searched for homology with the C-terminal sequence of the GDH α subunit of KS1 strain. As a result, amino acid sequences translated from two gene fragments showed high homologies (>90%). Each gene fragment was as short as 200 to 500 bp, so that sequences having high homologies with these sequences were searched from the genome database of Burkholderia cepacia J2315 strain by BLAST and the fragments were joined each other. As a result, a fragment of 3,110 bp was obtained. In the obtained nucleotide sequence, there existed an ORF that is presumed to be the C-terminus of the GDH and an ORF that is presumed to be cytochrome C structural gene of 1,275 bp (SEQ ID NO: 11). The amino acid sequence encoded by the ORF is shown in SEQ ID NO: 12. Results of comparison between the obtained nucleotide sequence of the J2315 strain and the nucleotide sequence of the α subunit of KS1 strain that has already been cloned indicate that in the downside of the α subunit, the nucleotide sequence having a high homology with the nucleotide sequnece encoding the signal peptide of cytochrome C of J2315 strain is contained.

From the above, the third ORF in the cloned fragment of Burkholderia cepacia KS1 strain obtained in Reference Example 1 (nucleotides 2386 et seq. of SEQ ID NO: 1) is presumed to encode the β subunit. The amino acid sequence at the N-terminus of the purified β subunit corresponds to the 5 amino acid residues translated by the nucleotide sequence consisting of nucleotides 2452 to 2466 in SEQ ID NO: 1, which also suggests that the aforementioned ORF encodes the β subunit.

<2> Amplification of β Subunit Structural Gene Using Inverse PCR Method (1) Culture of Microorganism Cell and Extraction of Genome Using 5 ml of complete medium (0.5% polypepton, 0.3% yeast extract, 0.5% NaCl), KS1 strain was cultured with shaking at 37° C. overnight. Genome was extracted from the obtained microorganism cells using GennomicPrep™ Cells and Tissue DNA Isolation Kit (Amersham Pharmacia Biotech). The method was performed in accordance with the attached manual. The obtained genome was subjected to phenol/chloroform treatment and precipitated with ethanol, and then dissolved in purified water.

(2) Cyclization of Genome Fragment

The genome extracted from the KS1 strain was digested with BamHI, EcoRI, HindIII, SmaI, SacI, and XhoI and the genome fragments were recovered by precipitation with ethanol. Then, 1 μg of genome digested with the restriction enzymes was subjected to ligation reaction using a DNA ligation kit (Takara Shuzo Co., Ltd.) at 16° C. overnight.

(3) PCR 50 pmol of forward primer (EF1 SEQ ID NO: 13) designed based on the nucleotide sequence in the N-terminal signal sequence region of the GDH β subunit of the KS1 strain, 50 pmol of reverse primer (ER1 SEQ ID NO: 14) (all the primers were synthesized by Invitrogen on consignment), 0.5 ml of LATaq (Takara Bio Co., Ltd.), 8 μl of dNTP solution, and 5 μl of 10×PCR buffer was added to purified water so as to have a total volume of 50 μl, and PCR was performed using a program temp control system PC-801 (ASTEC). The PCR reaction was performed under the following conditions: after 30 cycles of 94° C. for 5 minutes, 98° C. for 20 seconds, 62° C. for 30 seconds, 72° C. for 6 minutes, and 72° C. for 10 minutes.

When the genome digested with a restriction enzyme (SmaI) is used as a template, a fragment having a size of about 2.1 kbp was confirmed on Agarose electrophoresis.

<3> Sequencing of PCR-amplified Fragment (1) TA Cloning

After the aforementioned inverse PCR product was electrophoresed on Agarose gel, the band was cut out and purified using Gene clean II KIT (Bio101 inc.). The fragment was ligated to pGEM-T Vector using pGEMR-T and pGEMR-T EASY Vector Systems (Promega). *E. coli* DH5α was transformed with the ligated vector, and the transformant was cultured on an L-agar medium containing 50 µg/ml ampicillin, 40 µg/ml X-Gal, and 0.1 µM IPTG overnight. From the appeared colonies, white colonies were selected and cultured in an L medium containing 50 µg/ml ampicillin overnight, followed by extraction of plasmids from the cells by the alkali method.

(2) Preparation of Sequence Sample

The obtained plasmid was treated with RNase and 0.6 volume of 20% PEG6000/2.5 M NaCl was added thereto. The mixture was left to stand on ice for 1 hour. Thereafter, the mixture was centrifuged at 15,000 rpm and 4° C. for 15 minutes to obtain a pellet. The pellet was washed with 70% ethanol and dried in vacuum. The dried product was dissolved in purified water.

(3) Analysis of Nucleotide Sequence of DNA

The nucleotide sequence of the inserted fragment of the plasmid obtained in (2) was analyzed using ABI PRISM™ 310 Genetic Analyzer (PERKIN-ELMER Applied Biosystems). A portion of the sequence of the inserted fragment was determined from the multicloning site of the vector using M13 primer. As a result, the nucleotide sequnece containing the N-terminus of the β subunit that had been already analyzed was confirmed. Based on this sequence, primers were sequentially prepared and used to determine the nucleotide sequence of the inserted fragment. The result is shown in SEQ ID NO: 15. Further, the amino acid sequence encoded by the ORF in the nucleotide sequence is shown in SEQ ID NO: 16.

The β subunit has 425 amino acid residues in total, and from the comparison with the N-terminal amino acid sequence already obtained, 22 residues among them are considered to be a signal peptide. The molecular weight of the β subunit calculated based on the amino acid sequence is 45,276 Da and the molecular weight 42,731 Da of the portion excluding the signal peptide is substantially identical to the molecular weight 43 kDa of the GDH β subunit of the KS1 strain. In the amino acid sequence of the β subunit, linking motifs (SEQ ID NO: 18) that links with hem in cytochrome C were confirmed at 3 positions. The ORFs were located immediately downstream of the ORF of the structural gene of the α subunit, and a sequence that is presumed to be an SD sequence existed upstream of the initiation codon.

Homology search for the obtained amino acid sequence by BLAST showed overall high homologies; a 65% homology with cytochrome C subunit of oxidoreductase dehydrogenase derived from *Ralstonia solanacearum,* a 48% homology with a cytochrome C subunit of sorbitol dehydrogenase derived from *Gluconobacter oxydans,* a 44% homology with a cytochrome C subunit of gluconic acid dehydrogenase derived from *Eriwinia cypripedii,* and a 46.4% homology on an amino acid level with a cytochrome C subunit of 2-ketogluconic acid dehydrogenase derived from *Pantoea citrea.* Furthermore, the amino acid sequences of cytochromes C reserved a hem-linking motif (SEQ ID NO: 18).

The structural gene of the GDH β subunit of the KS1 strain has a homology of 92.0% on the nucleotide sequnece level and of 92.2% on an amino acid level with the structural gene of the GDH β subunit of the J2315 strain.

INDUSTRIAL APPLICABILITY

The present invention provides the GDH β subunit of a microorganism belonging to the genus *Burkholderia* and the DNA encoding it.

What is claimed is:

1. A recombinant DNA comprising:
   (a) a first nucleotide sequence as defined in the following (i) or (ii):
      (i) a DNA comprising the nucleotide sequence consisting of nucleotides 187 to 1398 of SEQ ID NO: 15;
      (ii) a DNA which is hybridizable with the nucleotide sequence consisting of nucleotides 187 to 1398 of SEQ ID NO: 15 under stringent conditions consisting of 1×SSC, 0.1% SDS, and 60° C., which encodes a cytochrome c subunit having a substitution, deletion, insertion or addition of 1 to 5 amino acid residues in amino acids 23 to 425 of SEQ ID NO: 16; and
   (b) a second nucleotide sequence encoding an α subunit of SEQ ID NO: 3 and a γ subunit of SEQ ID NO: 2 of glucose dehydrogenase of *Burkholderia cepacia*.

2. A recombinant vector comprising the DNA according to claim 1.

3. An isolated host cell transformed with the DNA according to claim 1.

4. A method of producing a glucose dehydrogenase complex, comprising culturing the cell according to claim 3 to produce a glucose dehydrogenase complex as an expression product of the DNA, and collecting the produced complex.

5. A recombinant DNA according to claim 1, further comprising a third nucleotide sequence consisting of nucleotides 121 to 187 of SEQ ID NO: 15.

6. A recombinant vector comprising the DNA according to claim 5.

7. An isolated host cell transformed with the recombinant vector according to claim 2.

8. An isolated host cell transformed with the DNA according to claim 5.

9. An isolated host cell transformed with recombinant vector according to claim 6.

10. A method of producing a glucose dehydrogenase complex, comprising culturing the cell according to claim 7 to produce a glucose dehydrogenase complex as an expression product of the DNA, and collecting the produced complex.

11. A method of producing a glucose dehydrogenase complex, comprising culturing the cell according to claim 8 to produce a glucose dehydrogenase complex as an expression product of the DNA, and collecting the produced complex.

12. A method of producing a glucose dehydrogenase complex, comprising culturing the cell according to claim 9 to produce a glucose dehydrogenase complex as an expression product of the DNA, and collecting the produced complex.

* * * * *